United States Patent
Sakamoto

(10) Patent No.: US 6,930,091 B2
(45) Date of Patent: Aug. 16, 2005

(54) PEPTIDES AND REMEDY FOR BONE DISEASES CONTAINING THE SAME AS ACTIVE INGREDIENT

(76) Inventor: Kenji Sakamoto, 25, Aza Kourokuzawa, Memeki, Yuuwa-machi, Kawabe-gun, Akita (JP), 010-12

(*) Notice: Subject to any disclaimer, the term of this patent is extended or adjusted under 35 U.S.C. 154(b) by 382 days.

(21) Appl. No.: 10/096,525

(22) Filed: Mar. 11, 2002

(65) Prior Publication Data

US 2004/0162415 A1 Aug. 19, 2004

Related U.S. Application Data

(63) Continuation of application No. 09/458,745, filed on Dec. 10, 1999, now Pat. No. 6,420,520, which is a continuation of application No. 08/930,776, filed as application No. PCT/JP96/00915 on Apr. 3, 1996, now Pat. No. 6,071,881.

(30) Foreign Application Priority Data

Apr. 3, 1995 (JP) ............................................. 7-101681

(51) Int. Cl.[7] ........................ A61K 38/10; A61K 38/16
(52) U.S. Cl. .......................................... 514/13; 514/14
(58) Field of Search ........................... 514/2, 8, 13, 14, 514/21; 530/300, 326, 327, 350, 395

(56) References Cited

U.S. PATENT DOCUMENTS 5,262,319 A    11/1993  Iwata et al. .............. 435/240.2
6,071,881 A *  6/2000  Sakamoto .................... 514/13
6,420,520 B1 * 7/2002  Sakamoto .................... 530/326

OTHER PUBLICATIONS

Alan H. Gorn et al., "Cloning, Characterization, and Expression of a Human Calcitonin Receptor from an Ovarian Carcinoma Cell Line " © *The American Society for Clinical Investigation, Inc.*, Nov. 1992, 1726–1735 (vol. 90) Massachusetts, Journal of Clinical Investigation.

Daniel R. Nussenzveig et al., "Inhibition of Inositol Phosphate Second Messenger Formation by Intracellular Loop One of a Human Calcitonin Receptor" *The Journal of Biological Chemistry*, Nov. 1994, 28123–28129 (vol. 269) USA.

* cited by examiner

*Primary Examiner*—Jeffrey Edwin Russel
(74) *Attorney, Agent, or Firm*—Brooks Kushman P.C.

(57) ABSTRACT

A new substance useful as a drug for the treatment of osteopathy is disclosed. The present invention provides a peptide and derivative thereof having an amino acid sequence SEQ ID NO: 1 designated hereunder as follows, wherein both of the peptide and derivative thereof having growth promotion effects and activity promotion effects on osteoblasts, as well as a drug having the peptide as an effective component for the treatment of osteopathy:

```
Lys Leu Thr Thr Ile Phe Pro Leu Asn     SEQ ID NO: 1
 1               5
              Trp Lys Tyr Arg Lys Ala Leu.
               10                  15
```

21 Claims, No Drawings

PEPTIDES AND REMEDY FOR BONE DISEASES CONTAINING THE SAME AS ACTIVE INGREDIENT

CROSS-REFERENCE TO RELATED APPLICATIONS

This is a continuation of prior application Ser. No. 09/458,745 filed on Dec. 10, 1999, entitled, "Novel Peptides And Remedy For Bone Diseases Containing The Same As Active Ingredient," now U.S. Pat. No. 6,420,520; which is a continuation of application Ser. No. 08/930,776, filed on Jan. 4, 1999, entitled, "Novel Peptides And Remedy For Bone Diseases Containing The Same As Active Ingredient", now U.S. Pat. No. 6,071,881; which was the National Stage of International Application No. PCT/JP96/00915, filed Apr. 3, 1996.

FIELD OF THE INVENTION

The present invention relates to a new drug containing the same as an effective component for treating osteopathy.

BACKGROUND OF THE INVENTION

It is well known that there are a number of physiological active substances in a human body, and that such substances are closely involved in the support of normal biological activities in a human body. Both of such physiological active substances of a human body and synthesized physiological active substances are showing possibilities of being new drugs as well as providing new insights into the development of new drugs. Therefore, the search for such physiological active substances is of utmost importance.

On the other hand, for the treatment of osteopathy such as osteoporosis, calcitonin, female hormone, and activated vitamin D3 and the like are currently used, the remedial effects thereof are not necessarily of satisfactory one.

SUMMARY OF THE INVENTION

The object of the present invention is to provide a new substance which is useful as a drug for the remedy of osteopathy.

The present inventors found, while conducting various experiments to search for a substance which promotes the activities of osteoblasts, a new peptide having foregoing effects on osteoblasts which is involved in the bone formation, and the present invention was made through such a finding.

In other words, the present invention provides a peptide and a derivative thereof, said peptide having an amino acid sequence designated by the sequence number 1 shown in the sequence table attached herewith, wherein both of said peptide and said derivative thereof having growth promotion effects and activity promotion effects on osteoblasts. In another aspect of the present invention, it provides a drug having said peptide of the present invention as an effective component for treating osteopathy.

The present invention is further explained in detail hereunder.

BEST MODE FOR CARRYING OUT THE INVENTION

The peptide of the present invention has basically an amino acid sequence designated by sequence number 1 shown in the sequence table attached herewith.

Furthermore, with the scope of the present invention, in addition to said peptide having an amino acid sequence designated by the sequence number 1 shown in the sequence table attached herewith, a derivative of said peptide is included, wherein said derivative having growth promotion effects and activity promotion effects on osteoblasts. For example, any "derivative peptide" referred to in the present invention may include any derivative of said peptide obtained by any chemical modification thereof which may not impede any of said effects. For example, it is well known that by replacing the carboxyl radical at the C end of a peptide with an amino radical, the stability thereof in a human body is increased, and any of such chemically modified peptide is included in the scope of the present invention.

Still further, it is well known to anyone skilled in the art that, in case of a peptide which generally has physiological activity, even when some of the amino acids thereof are replaced by other amino acids, when some amino acids are added thereto, or when some of the amino acids are deleted therefrom, there are cases where the physiological activity is maintained. Therefore, in case of the scope of the present invention, the "derivative peptide" includes any peptide wherein some of the amino acids which form said peptide having an amino acid sequence designated by the sequence number 1 are replaced by some other amino acids, wherein some amino acids are added thereto, or wherein there are some amino acids deleted therefrom, and furthermore, among such derivative peptides, any peptide having growth promotion effects and activity promotion effects on osteoblasts are included in the scope of the present invention. For example, the scope of the present invention includes a peptide where not more than 5 amino acids are added, replaced or deleted, or a peptide wherein the degree of homology of the amino acid sequence is not less than 70% and said peptide having growth promotion effects and activity promotion effects on osteoblasts. Furthermore, whether a derivative of a peptide has growth promotion effects and activity promotion effects on osteoblasts may be examined by the method of Examples 2 and 4 described hereunder.

The peptide of the present invention designated by the sequence number 1 has a rather small number of amino acid components, with such number being 16, it may be easily synthesized by a chemical synthesizing method of any known method. For example, it may be easily produced by using a commercially available peptide synthesizing machine. It may also be easily produced by any of known generic engineering methods, wherein a DNA encoding said amino acid sequence is synthesized by using a DNA synthesizing machine, followed by inserting said DNA into the cloning portion of a commercially available cloning vector thereby transforming the host microorganism, followed further by culturing the same.

As has been experimentally confirmed in the examples described hereunder, the peptide of the present invention has growth promotion effects and activity promotion effects on osteoblasts. Therefore, the peptide of the present invention is useful as a drug for the treatment of osteopathy such as osteoporosis. Osteopathy which can be cured by the peptide of the present invention may be found, for example, in osteomalacia and the like other than osteoporosis.

Because the molecular weight of the peptide of the present invention is relatively low, it may be intravenously administered, hypodermically administered, intramuscularly administered, as well as orally administered or percutaneously administered after the dosage is prepared by any of the known method.

Although the amount of dosage may be appropriately decided depending on the patient's condition, it may be generally in the order of 0.1 to 10 mg of the peptide of the present invention per an adult per each day.

Furthermore, in case of intravenous administration, hypodermic administration or intramuscular administration, the peptide of the present invention is preferably administered after dissolving the same into a weak acid buffer solution such as a citric buffer solution (pH 4~6) or acetic buffer solution (pH 4~6). In such a case, the concentration of the peptide in the buffer solution is generally in the order of 0.1 mg/ml~10 mg/ml. In case of oral administration or percutaneous administration, the peptide is preferably dissolved into a fat-soluble substance (for example, petrolatum and the like) to facilitate the increase of absorption characteristics. In such a case, the concentration of the peptide of the present invention is generally in the order of from 0.1 mg/ml to 100 mg/ml.

EXAMPLES

The present invention is further described in detail with reference to examples. However, the scope of the present invention is not restricted to the examples described hereunder.

Example 1

A peptide having an amino acid sequence designated by the sequence number 1 was synthesized by using a commercially available peptide synthesizing machine.

Example 2

Effects on Growth Promotion of Osteoblasts

ROS cells, which are osteoblasts, obtained from a rat (source: ATCC) are cultured on a F10 medium containing 10% of the serum of a calf embryo, followed by a growing in a thermostat being set at 37° C. and under a humidification by 5% carbon dioxide gas. Seeding of 1×10⁵ cells/well on a culture plate with 24 wells was effectuated after trypsinization, followed by replacing said medium with a F10 medium having 1% of the serum of a calf embryo when the former became confluent, and thereafter it was cultured for 24 hours. Then, the peptide of the present invention produced in Example 1 of this invention was dissolved in a F10 medium having 1% of the serum of a calf embryo, and it was added to wells while the amount thereof being varied, followed by continuation of the culture process for another 24 hours. After the culture process, the cell growth promotion effects of the present peptide was measured by MTT assay to obtain the growth promotion effects in comparison with the untreated group. MTT assay and the calculation of the rate of growth promotion was, in effect, carried out as follows. According to the procedure of MTF-Cell-Growth Assay kit commercially available from Funakoshi Co., Ltd., after adding the present substance to the wells while the amount thereof being varied and followed by leaving the same for a whole day, the number of living cells were counted by calorimetric analysis by using a phenomenon wherein MTT (3–4, 5-Dimethylthiazol-2-YL)-2,5-Diphenyl Tetrazolium Bromide is cleaved to produce formazan having dark blue color by an enzyme present in the mitocondrion of a living cell. The calorimetric results of the group obtained by adding varying amount of the present substance thereto, while the control group to which none of the present substance was added being as 100%, are shown as follows. The results are shown in the following Table 1.

TABLE 1

| Amount of Peptide Added (μg/well) | Rate of Growth Promotion (%) |
|---|---|
| 0 | 100.0 |
| 0.001 | 109.6 |
| 0.01 | 110.5 |
| 0.1 | 636.2 |
| 1.0 | 1317.1 |

As can be seen from Table 1, it was confirmed that the peptide of the present invention provides growth promotion effects on osteoblasts. Therefore, it is considered that the peptide of the present invention is related to an increase of the amount of bone, and it is useful for the treatment of osteopathy such as osteoporosis and the like.

Example 3

Existence of a Receptor for the Peptide of the Present Invention on an Osteoblast Because it was found that the peptide of the present invention has growth promotion effects on osteoblasts, it can be inferred that osteoblasts have receptors for the present peptides. If there is any receptor, the present peptide can be considered to be the fundamental substance for the living organisms or cells, and further analysis was carried out to find out whether the osteoblast has any receptor or not.

The peptide obtained in Example 1 was marked by biotin, and then, the present peptide after being marked to a certain degree was added to ROS cells cultured in the same way as that of Example 2, wherein the present peptide without any marking was dissolved, to effectuate competing reaction, into a F10 medium having 10% of the serum of a calf embryo, followed by adding the same, while varying the amount thereof, to said cells to see the competing reaction. The actual process of this experiment was as follows. According to the procedures of a protein bionizing and labeling kit available from UMILON, the present peptide was biotinized, and then, a certain amount of biotinized peptide was added to a certain number of cells seeded in wells, then from 0 to 0.512 μg/well of unlabeled peptide was added to each cell to effectuate the competing reaction for 6 hours, and thereafter, the cell was washed by PBS and then the coloration reaction, which was caused by peroxidase labeled with streptoabidin reacting with biotinized peptide bonded to receptors present on the cell surface, was observed. When any receptor for the present peptide is present on the cell surface, there is a reaction competing with the unlabeled peptide whereby the coloration degree is decreased. The results are shown in Table 2 hereunder.

TABLE 2

| Amount of Unlabeled Peptide Added (μg/well) | Ratio to the Labeled Peptide (%) |
|---|---|
| 0 | 100 |
| 0.032 | 98.4 |
| 0.064 | 86.5 |
| 0.128 | 79.6 |
| 0.256 | 34.1 |
| 0.512 | 29.5 |

As shown in Table 2 above, because the ratio to the added labeled peptide varies depending on the amount of unlabeled peptide, it is obvious that the osteoblast has receptors for the present peptide, and it is further inferred that the present substance has a fundamental role.

Tests on Acute Toxicity

By using the peptide prepared in Example 1, its acute toxicity was tested on ddy male mice (with the body weight ranging from 40 to 45 g). The present peptide was dissolved in a physiological saline (pH 6.0) and the solution thereof was administered intravenously into a vein in the tail of each mouse, and observation was made for 14 days. The dosage amount was set respectively at 1, 10, and 100 µg/kg. The results are shown in Table 3 hereunder.

TABLE 3

| Dosage Amount (µg/kg) | Number of Deceased Mice |
| --- | --- |
| 1 | 0/5 |
| 10 | 0/5 |
| 100 | 0/5 |

As can be seen from the above table, there was not deceased mouse observed up to the dosage amount of 100 µg/kg.

INDUSTRIAL APPLICABILITY

A new peptide is provided by the present invention. The peptide of the present invention has, as has been experimentally confirmed by the above examples, growth promotion effects and activity promotion effects on osteoblasts, and it has been made obvious that such peptide has effects as a drug for the treatment of osteopathy.

2. The method of claim 1 wherein the disease or disorder is osteoporosis.

3. The method of claim 1 wherein the disease or disorder is osteomalacia.

4. The method of claim 1 wherein the treatment is administered intravenously, intramuscularly, hypodermically, orally or percutaneously.

5. The method of claim 1 wherein one or more amino acids of said peptide have been chemically modified.

6. The method of claim 5 wherein the chemical modification is the replacement of the carboxyl radical at the C-terminus of the peptide with an amino radical.

7. The method of claim 5 wherein the modification is to one or more of the amino acid side chains.

8. A method for the treatment of a patient having a bone disease or disorder comprising administering to the patient a therapeutically effective amount of a peptide having no more than five amino acid residues which are different from the peptide of SEQ. ID. NO: 1.

9. The method of claim 8 wherein the disease or disorder is osteoporosis.

10. The method of claim 8 wherein the disease or disorder is osteomalacia.

11. The method of claim 8 wherein the treatment is administered intravenously, intramuscularly, hypodermically, orally or percutaneously.

12. The method of claim 8 wherein one or more amino acids of said peptide have been chemically modified.

13. The method of claim 12 wherein the chemical modification is the replacement of the carboxyl radical at the C-terminus of the peptide with an amino radical.

14. The method of claim 12 wherein the modification is to one or more of the amino acid side chains.

15. A method of treating a condition accompanied or caused by a modification of the number or activation state of

---

SEQUENCE TABLE

Sequence Number: 1
Sequence Length: 16
Type of Sequence: Amino Acid
Sequence:
Lys Leu Thr Thr Ile Phe Pro Leu Asn Trp Lys Tyr Arg Lys Ala Leu
1               5                   10                  15

---

---

What is claimed is:

1. A method for the treatment of a patient having a bone disease or disorder comprising administering to the patient a therapeutically effective amount of a peptide consisting of at least 12 and no more than 21 amino acid residues in length and having at least 70% homology to the sequence of SEQ. ID. NO: 1.

osteoblasts comprising administering to a host in need of such treatment an effective amount of a peptide consisting of at least 12 and no more than 21 amino acid residues in length and having at least 70% homology to the sequence of SEQ. ID. NO: 1.

16. The method of claim 15 wherein the disease or disorder is osteoporosis.

17. The method of claim 15 wherein the disease or disorder is osteomalacia.

18. The method of claim 15 wherein the treatment is administered intravenously, intramuscularly, hypodermically, orally or percutaneously.

19. The method of claim 15 wherein one or more amino acids of said peptide have been chemically modified.

20. The method of claim 19 wherein the chemical modification is the replacement of the carboxyl radical at the C-terminus of the peptide with an amino radical.

21. The method of claim 19 wherein the modification is to one or more of the amino acid side chains.

* * * * *

SEQUENCE LISTING

<160> NUMBER OF SEQ ID NOS: 1

<210> SEQ ID NO 1
<211> LENGTH: 16
<212> TYPE: PRT
<213> ORGANISM: Rattus rattus

<400> SEQUENCE: 1

Lys Leu Thr Thr Ile Phe Pro Leu Asn Trp Lys Tyr Arg Lys Ala Leu
1               5                   10                  15